United States Patent
Noguchi

(10) Patent No.: US 9,817,226 B2
(45) Date of Patent: Nov. 14, 2017

(54) ENDOSCOPE OBJECTIVE OPTICAL SYSTEM

(71) Applicant: OLYMPUS CORPORATION, Hachioji-shi, Tokyo (JP)

(72) Inventor: Azusa Noguchi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/358,768

(22) Filed: Nov. 22, 2016

(65) Prior Publication Data

US 2017/0071449 A1 Mar. 16, 2017

Related U.S. Application Data

(63) Continuation of application No. PCT/JP2015/075249, filed on Sep. 4, 2015.

(30) Foreign Application Priority Data

Sep. 22, 2014 (JP) ................. 2014-192404

(51) Int. Cl.
*G02B 23/24* (2006.01)
*G02B 9/12* (2006.01)
(Continued)

(52) U.S. Cl.
CPC .......... *G02B 23/243* (2013.01); *A61B 1/0019* (2013.01); *A61B 1/00096* (2013.01);
(Continued)

(58) Field of Classification Search
CPC .......... G02B 23/243; G02B 9/12; G02B 9/60; G02B 13/04; G02B 23/24; G02B 23/2407;
(Continued)

(56) References Cited

U.S. PATENT DOCUMENTS 4,059,344 A 11/1977 Yamasita
5,703,724 A * 12/1997 Miyano ................. G02B 23/243
359/644
(Continued)

FOREIGN PATENT DOCUMENTS

EP 2420880 A1 2/2012
EP 2477053 A1 7/2012
(Continued)

OTHER PUBLICATIONS

International Search Report (ISR) and Written Opinion dated Dec. 1, 2015 issued in International Application No. PCT/JP2015/075249.

*Primary Examiner* — Jordan Schwartz
(74) *Attorney, Agent, or Firm* — Holtz, Holtz & Volek PC

(57) ABSTRACT

Provided is an endoscope objective optical system including, in order from an object side, a first group having negative refractive power, a second group having positive refractive power, and a third group having positive refractive power. The second group is provided so as to be movable in an optical-axis direction. The following conditional expression is satisfied, $9 < f2/fa < 16$ (1)

where f2 is a focal length of the second group, and fa is a focal length of the entire system in the normal observation state.

3 Claims, 18 Drawing Sheets

(51) Int. Cl.
  *A61B 1/00* (2006.01)
  *G02B 13/18* (2006.01)
  *G02B 23/26* (2006.01)
  *G02B 7/04* (2006.01)
  *G02B 13/04* (2006.01)

(52) U.S. Cl.
  CPC ...... *A61B 1/00188* (2013.01); *A61B 1/00197* (2013.01); *G02B 7/04* (2013.01); *G02B 9/12* (2013.01); *G02B 13/04* (2013.01); *G02B 13/18* (2013.01); *G02B 23/2446* (2013.01); *G02B 23/26* (2013.01)

(58) Field of Classification Search
  CPC ............ G02B 23/2415; G02B 23/2423; G02B 23/2438; A61B 1/0019; A61B 1/00188; A61B 1/00163; A61B 1/00197
  USPC .................................................. 359/659–661
  See application file for complete search history.

(56) References Cited

U.S. PATENT DOCUMENTS

| | | | |
|---|---|---|---|
| 6,327,101 B1 | 12/2001 | Miyano | |
| 2001/0016680 A1 | 8/2001 | Minami et al. | |
| 2002/0055669 A1 | 5/2002 | Konno | |
| 2003/0117716 A1 | 6/2003 | Sekita | |
| 2008/0180809 A1 | 7/2008 | Igarashi | |
| 2009/0161234 A1* | 6/2009 | Sasamoto | G02B 23/2407 359/717 |
| 2010/0312057 A1 | 12/2010 | Konno | |
| 2011/0211267 A1 | 9/2011 | Takato | |
| 2012/0057251 A1 | 3/2012 | Takato | |
| 2012/0147164 A1* | 6/2012 | Sasamoto | A61B 1/00188 348/65 |
| 2012/0307374 A1 | 12/2012 | Kato et al. | |
| 2013/0155212 A1 | 6/2013 | Kamo | |
| 2013/0217965 A1 | 8/2013 | Sasamoto | |
| 2015/0042773 A1 | 2/2015 | Uzawa et al. | |
| 2015/0268460 A1 | 9/2015 | Takada | |

FOREIGN PATENT DOCUMENTS

| | | |
|---|---|---|
| EP | 2634614 A1 | 9/2013 |
| EP | 2706391 A1 | 3/2014 |
| EP | 2960701 A1 | 12/2015 |
| JP | 55015005 B2 | 4/1980 |
| JP | 2000330015 A | 11/2000 |
| JP | 2001166203 A | 6/2001 |
| JP | 2001269306 A | 10/2001 |
| JP | 2002028126 A | 1/2002 |
| JP | 2003050352 A | 2/2003 |
| JP | 2008107391 A | 5/2008 |
| JP | 4819969 B2 | 11/2011 |
| JP | 4934233 B2 | 5/2012 |
| JP | 2012247689 A | 12/2012 |
| WO | 2010119640 A1 | 10/2010 |
| WO | 2011070930 A1 | 6/2011 |
| WO | 2012169369 A1 | 12/2012 |
| WO | 2013021744 A1 | 2/2013 |
| WO | 2014088104 A1 | 6/2014 |
| WO | 2014129089 A1 | 8/2014 |

* cited by examiner

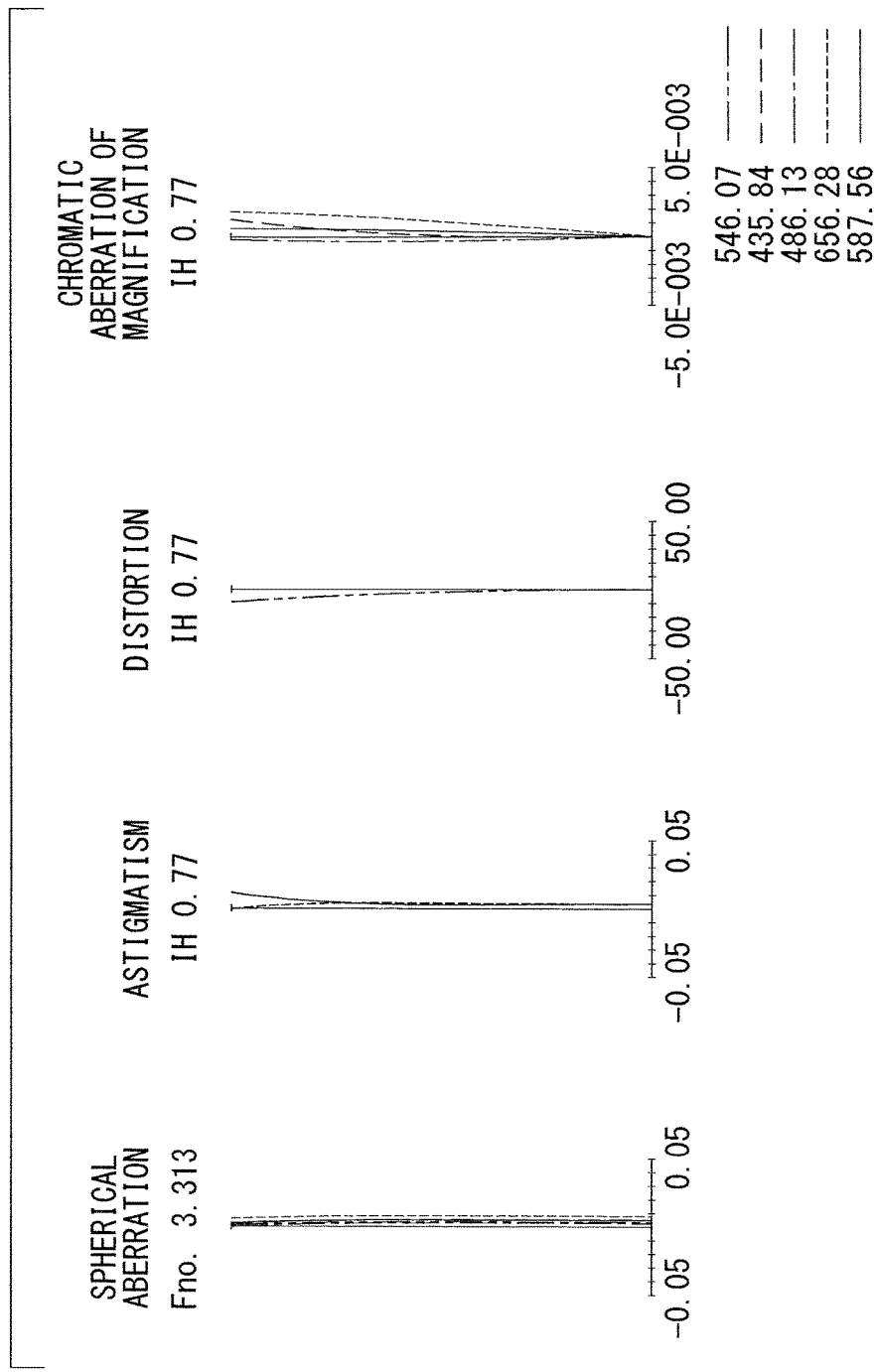

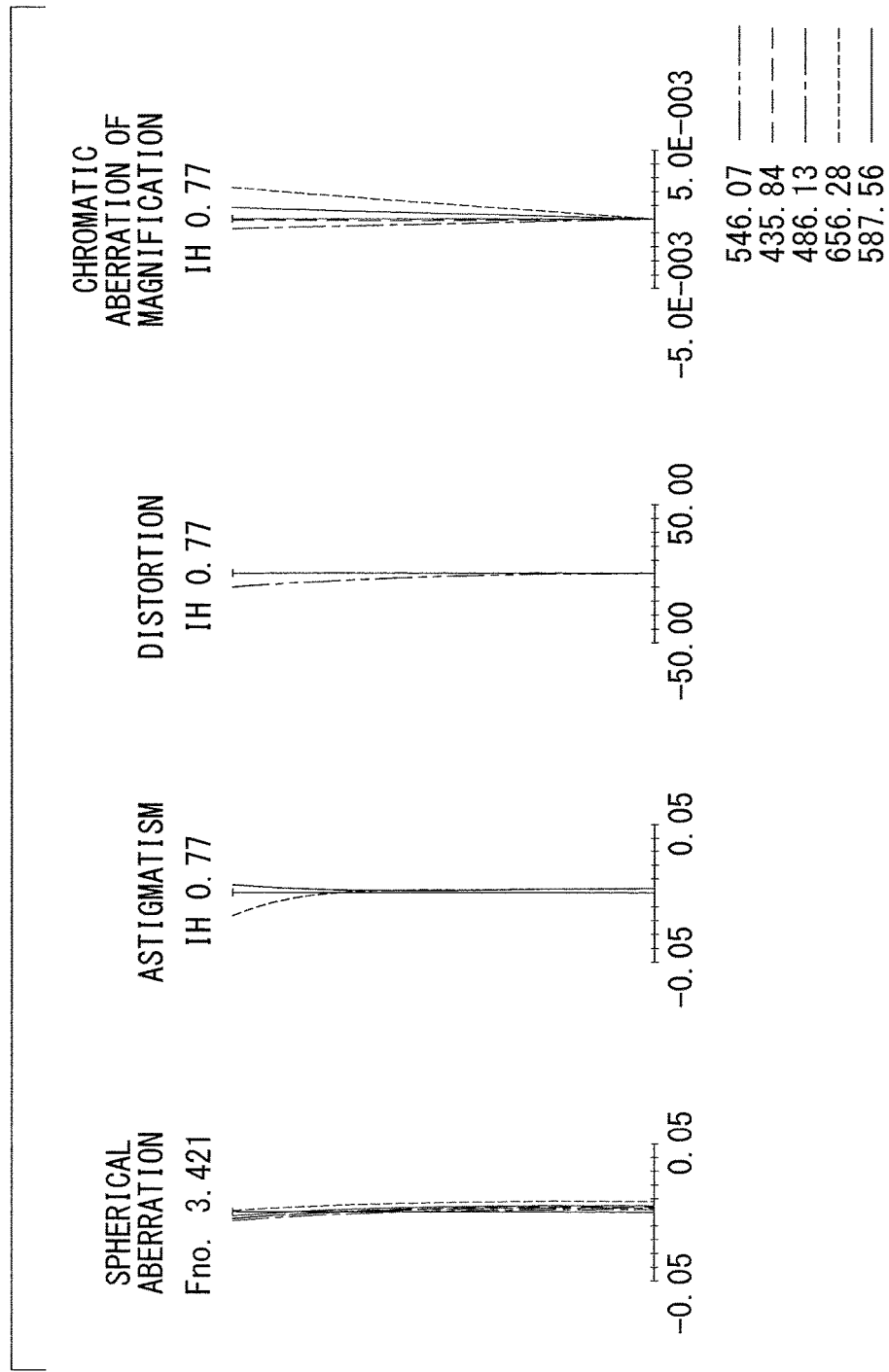

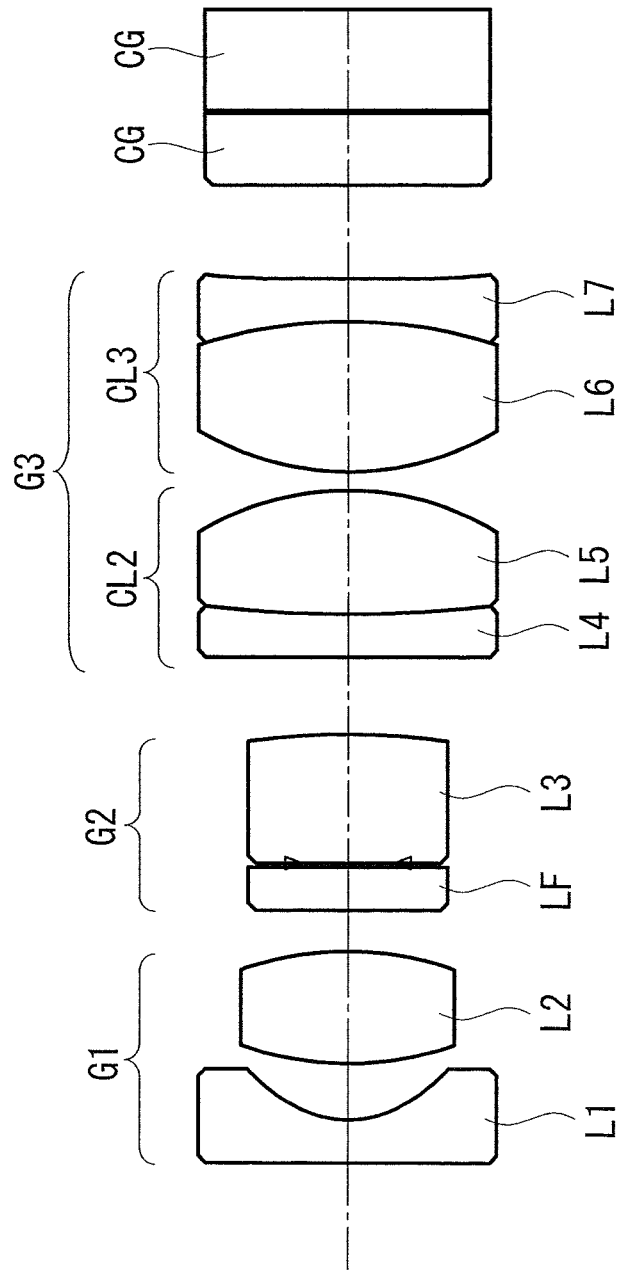

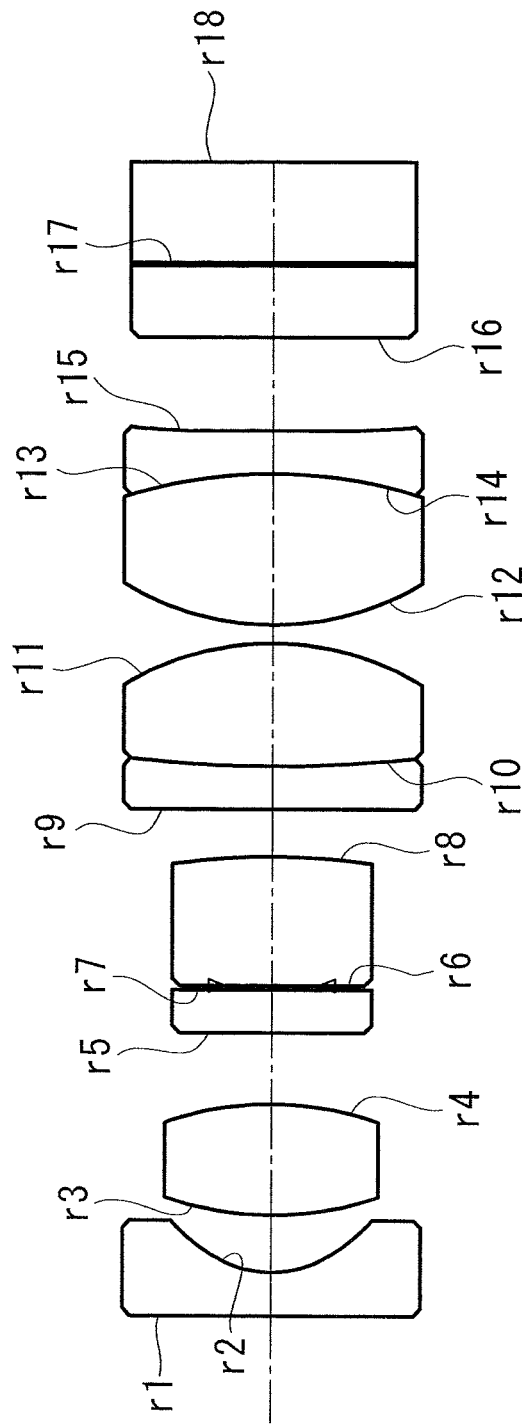

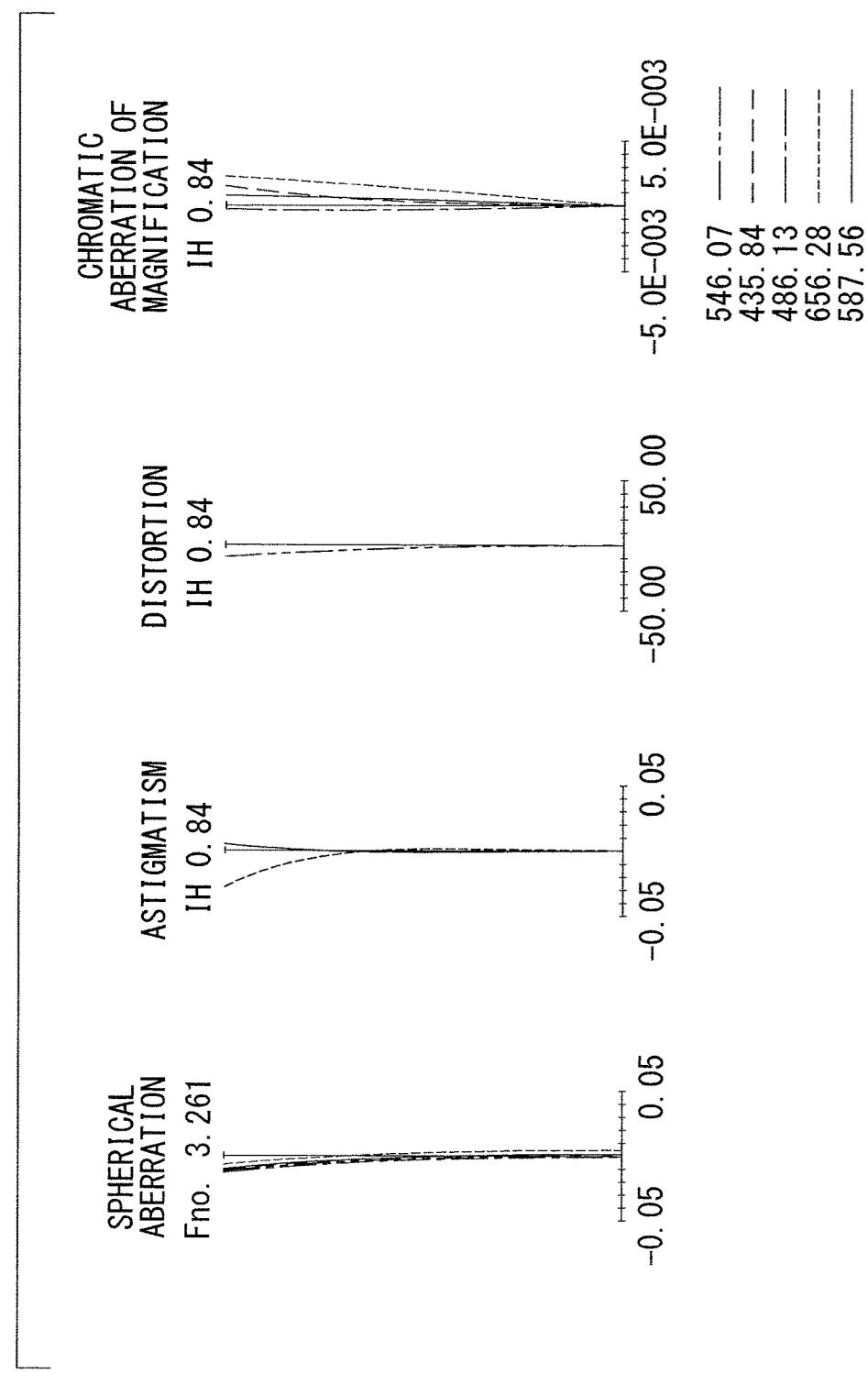

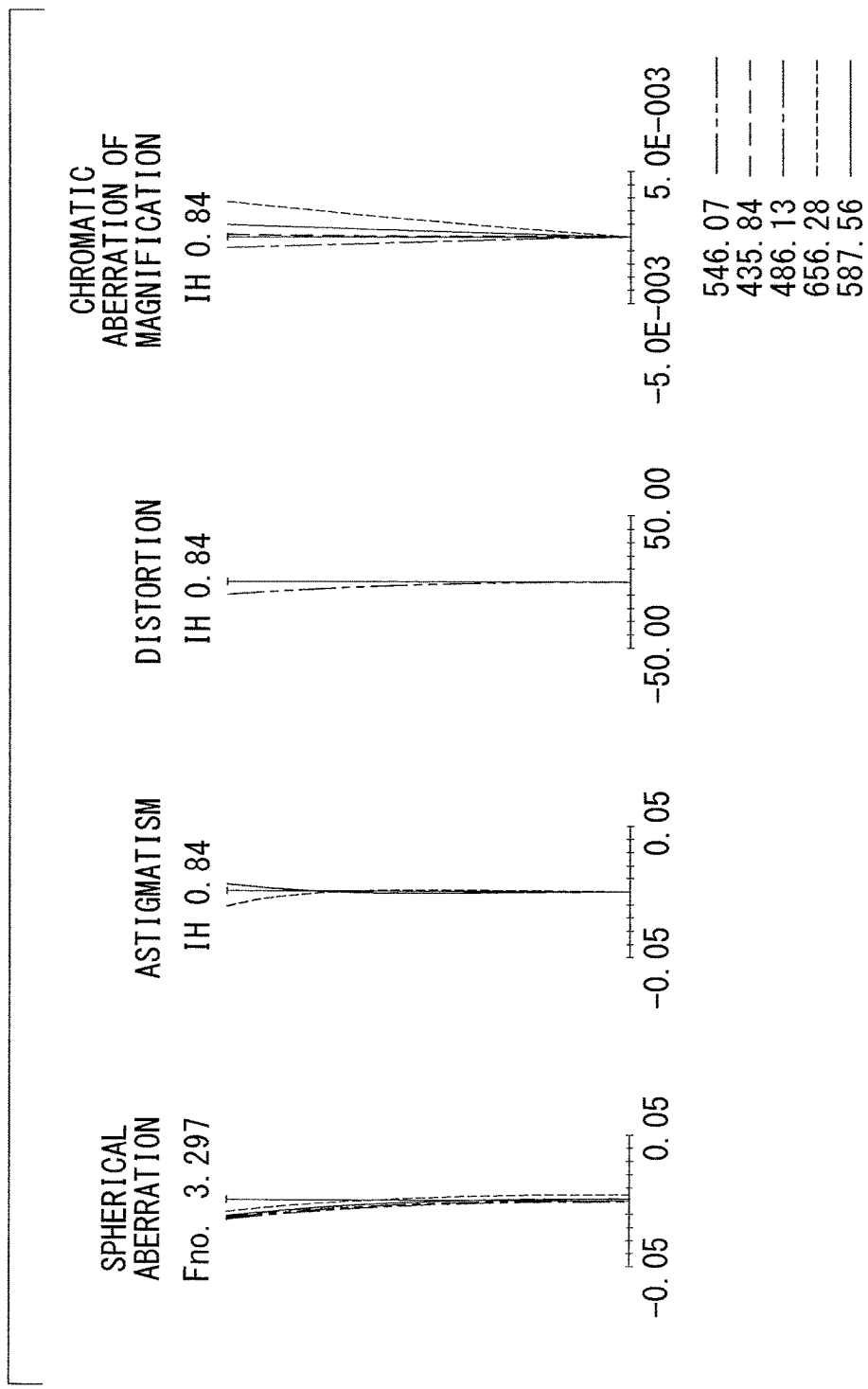

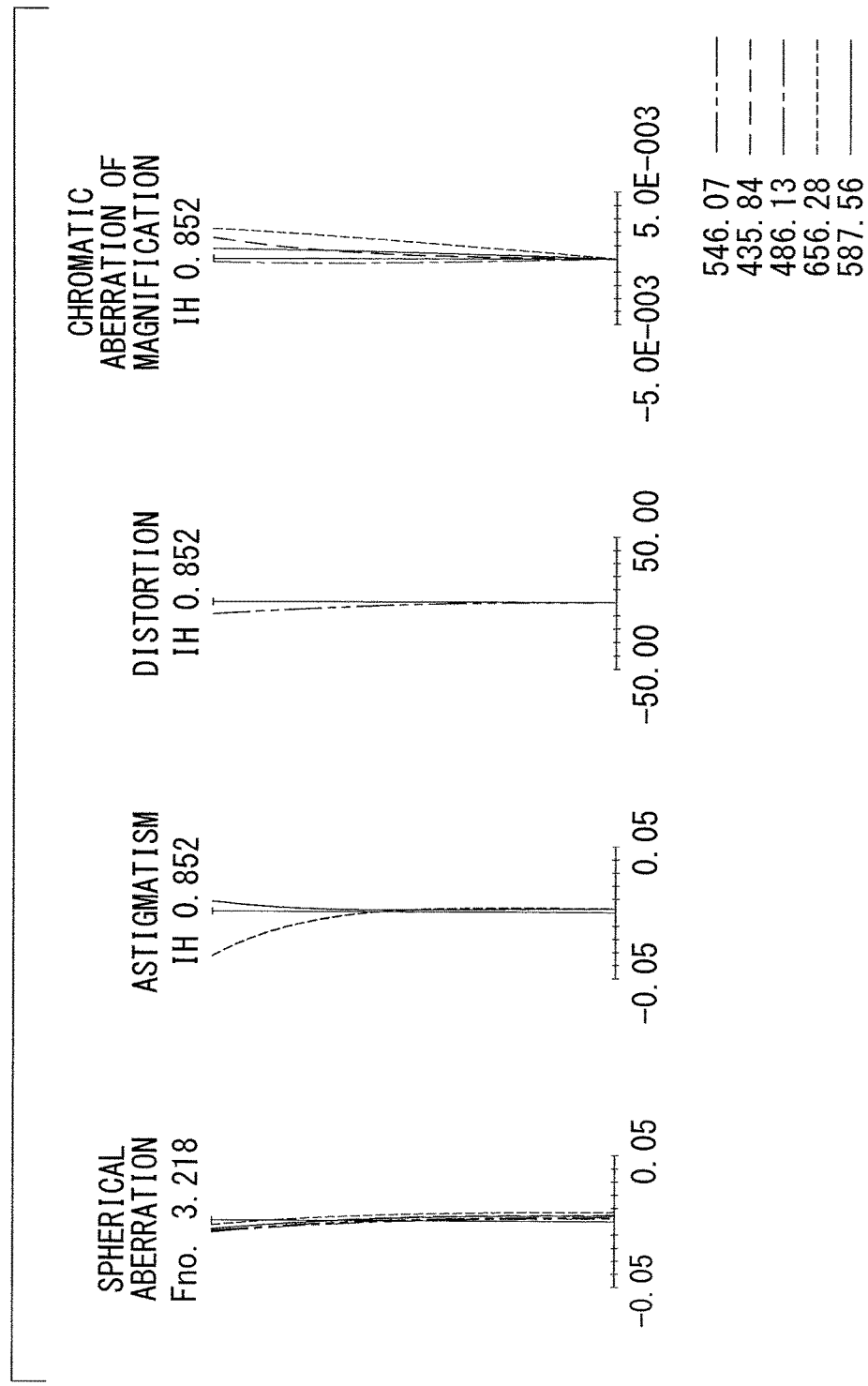

ENDOSCOPE OBJECTIVE OPTICAL SYSTEM

CROSS-REFERENCE TO RELATED APPLICATIONS

This is a continuation of International Application PCT/JP2015/075249, with an international filing date of Sep. 4, 2015, which is hereby incorporated by reference herein in its entirety. This application claims the benefit of Japanese Patent Application No. 2014-192404, the content of which is incorporated herein by reference.

TECHNICAL FIELD

The present invention relates to an objective optical system and, in particular, to an endoscope objective optical system that is applied to a medical endoscope and that has a focusing function.

BACKGROUND ART

In recent years, a reduction in the size of endoscopes and an improvement in the image quality thereof have progressed from the standpoint of relieving the burden on patients, improvements in diagnostic accuracy, etc. Thus, high-pixel-count and compact imaging devices have been developed as endoscope imaging devices (for example, CCD, CMOS, etc.). In such imaging devices, in order to increase the number of pixels while maintaining or reducing the size thereof, each pixel and the pixel pitch are reduced. With these reductions, it is also necessary to reduce the Fno. of an endoscope objective optical system in order to prevent image degradation caused by diffraction.

Incidentally, in an objective optical system, the observation depth is narrowed when the Fno. is reduced. Thus, various endoscope objective optical systems having a focusing function in order to obtain a desired observation depth have been proposed (for example, PTL 1 to PTL 6). In performing observation by using such an endoscope objective optical system, at the time of transition from normal observation to close observation, it is preferred that only the observation distance be changed, and that the change in the angle of view be small.

CITATION LIST

Patent Literature

{PTL 1} Japanese Examined Patent Application, Publication No. Sho 55-15005
{PTL 2} Japanese Unexamined Patent Application, Publication No. 2000-330015
{PTL 3} Japanese Unexamined Patent Application, Publication No. 2002-28126
{PTL 4} Japanese Unexamined Patent Application, Publication No. 2008-107391
{PTL 5} Publication of Japanese Patent No. 4934233
{PTL 6} Publication of Japanese Patent No. 4819969

SUMMARY OF INVENTION

An aspect of the present invention is directed to an endoscope optical system of the present invention including, in order from an object side, a first group having negative refractive power, a second group having positive refractive power, and a third group having positive refractive power, wherein the second group moves in an optical-axis direction to perform focusing for a normal observation state and a close observation state; and the following conditional expression is satisfied, $$9 < f2/fa < 16 \qquad (1)$$

where f2 is a focal length of the second group, and fa is a focal length of the entire system in the normal observation state.

BRIEF DESCRIPTION OF DRAWINGS

FIG. 3A is an aberration curve diagram of the endoscope objective optical system according to Example 1 of the present invention, in the normal observation state.

FIG. 3B is an aberration curve diagram of the endoscope objective optical system according to Example 1 of the present invention, in the close observation state.

FIG. 6 is a sectional view showing the overall configuration of an endoscope objective optical system according to a second embodiment of the present invention.

FIG. 7B is a sectional view of the endoscope objective optical system shown in FIG. 7A, in the close observation state.

FIG. 8A is an aberration curve diagram of an endoscope objective optical system according to Example 3 of the present invention, in the normal observation state.

FIG. 8B is an aberration curve diagram of the endoscope objective optical system according to Example 3 of the present invention, in the close observation state.

FIG. 10A is an aberration curve diagram of the endoscope objective optical system according to Example 4 of the present invention, in the normal observation state.

DESCRIPTION OF EMBODIMENTS

First Embodiment

An endoscope objective optical system according to a first embodiment of the present invention will be described below with reference to the drawings.

Figure 1:
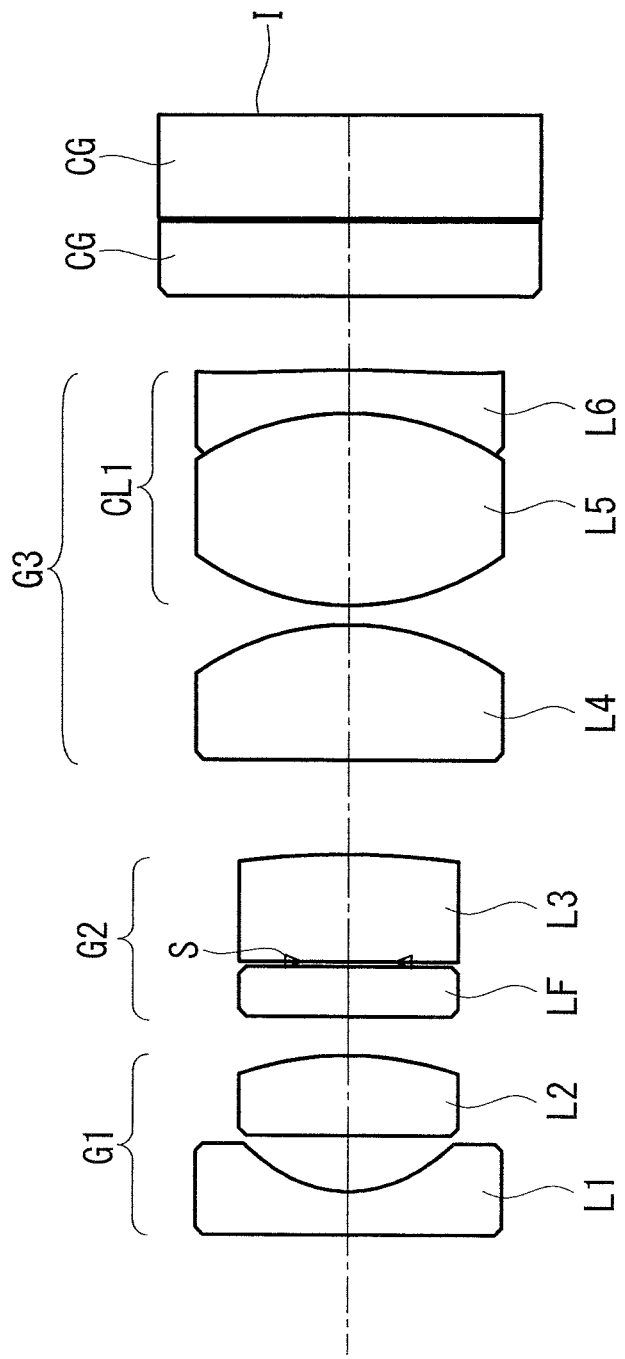
FIG. 1 is a sectional view showing the overall configuration of an endoscope objective optical system according to a first embodiment of the present invention.

As shown in FIG. 1, the endoscope objective optical system is provided with, in order from an object side, a first group G1 having negative refractive power, a second group G2 having positive refractive power, and a third group G3 having positive refractive power.

The first group G1 has, in order from the object side, a first lens L1 that is a negative plano-concave lens and a second lens L2 that is a positive plano-convex lens.

The second group G2 has a third lens L3 that is a plano-convex lens. Furthermore, the second group G2 has an aperture stop S at the object side of the third lens L3 and further has a light filter LF at the object side of the aperture stop S. The endoscope objective optical system performs focusing with respect to a change in object distance by moving the second group G2 in the optical-axis direction, thus making it possible to perform normal observation and close observation.

The third group G3 has, in order from the object side, a fourth lens that is a positive plano-convex lens and a combined lens CL1 in which a positive fifth lens and a negative sixth lens are combined. An imaging device in which a cover glass CG is bonded to an imaging surface is disposed at an imaging-plane side of the endoscope objective optical system.

Then, the endoscope objective optical system is configured so as to satisfy the following conditional expressions (1) to (3).

$$9 < f2/fa < 16 \quad (1)$$

where f2 is a focal length of the second group, and fa is a focal length of the entire system in a normal observation state.

$$0.2 < l/fa < 0.3 \quad (2)$$

where l is a movement distance of the second group associated with focusing, and fa is the focal length of the entire system in the normal observation state.

$$1.3 < d0a/d0b < 3.5 \quad (3)$$

where d0a is an object distance in the normal observation state, and d0b is an object distance in the close observation state.

In this way, according to this embodiment, the endoscope objective optical system is constituted by: the first group G1, which has negative refractive power; the second group G2, which has positive refractive power and which is provided with the aperture stop at the object side thereof; and the third group G3, which has positive refractive power, and also satisfies the conditional expressions (1) to (3). Therefore, a fluctuation in the angle of view at the time of focusing is suppressed, and an error caused by variations among parts is suppressed, thereby facilitating the focus adjustment work and making it possible to reduce the variation in the observation depth. Furthermore, the movement distance of the second group is made to fall within an appropriate range to allow the entire length of the endoscope objective optical system to be an appropriate length, thereby not impairing the operability of the endoscope.

Furthermore, the second group G2 is formed of the third lens L3, which is a single plano-convex lens, and the aperture stop S is disposed so as to be in contact with a plane surface of the third lens (piano-convex lens), thereby requiring no frame for holding the stop, facilitating the assembly, and making it possible to reduce the error in the position of the aperture stop in the endoscope objective optical system.

EXAMPLES

Next, Example 1 and Example 2 of the endoscope objective optical system of the above-described first embodiment will be described with reference to FIG. 2A to FIG. 5B.

In lens data to be described in each Example, r indicates the radius of curvature (unit mm), d indicates the intersurface spacing (mm), Ne indicates the refractive index at the e-line, and vd indicates the Abbe number.

Furthermore, in data related to an aspheric surface, an aspherical shape is defined by the following mathematical expression.

Note that, in the following mathematical expression, k is the constant of the cone, r is the radius of curvature, and ac4 and ac6 are fourth-order and sixth-order aspherical coefficients, respectively.

$$z = \frac{r \times y^2}{1 + \sqrt{1 - (k+1) \times r^2 \times y^2}} + (ac4 \times y^4) + (ac6 \times y^6)$$

Example 1

Figure 2A:
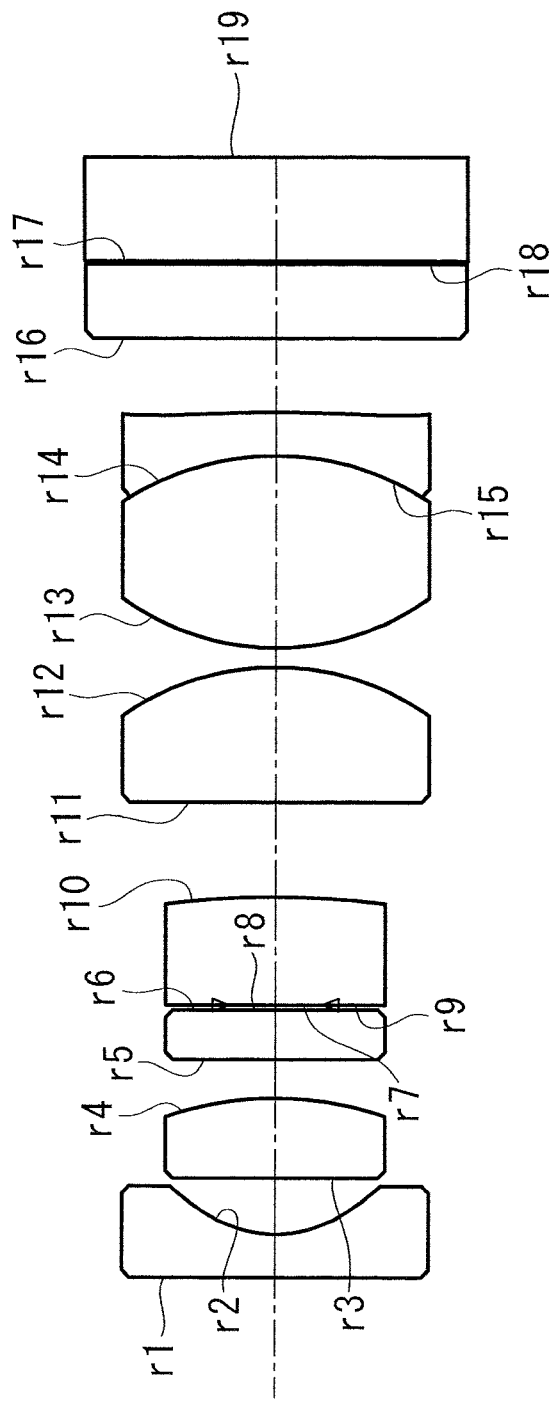
FIG. 2A is a sectional view showing the overall configuration of an endoscope objective optical system according to Example 1 of the present invention, in a normal observation state.
Figure 2B:
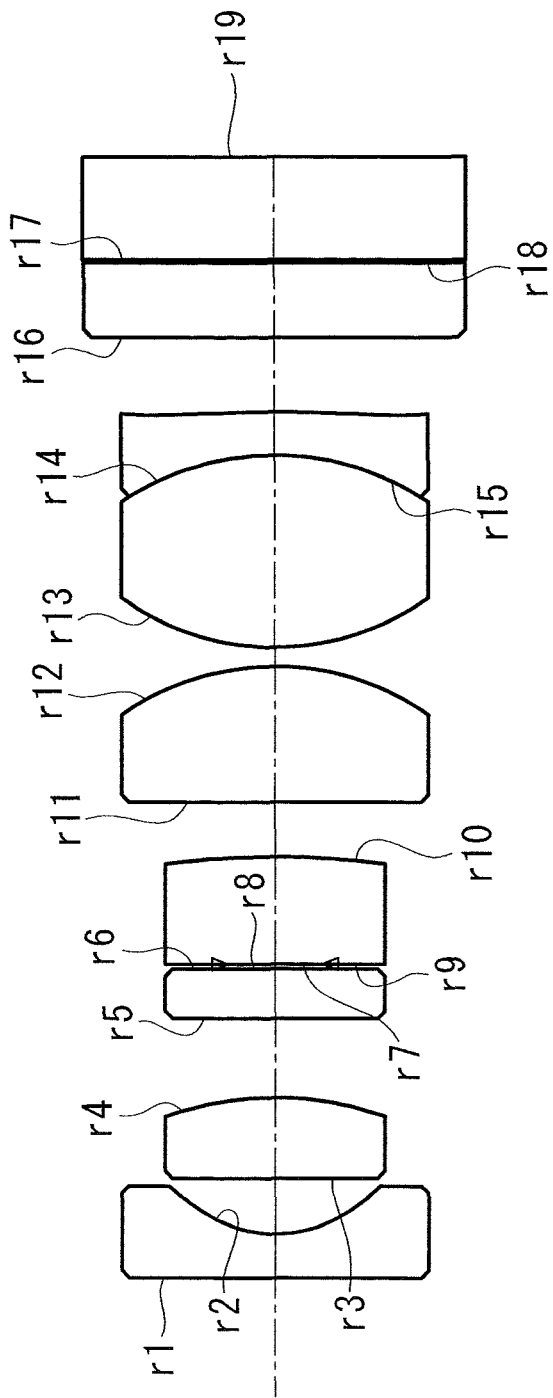
FIG. 2B is a sectional view of the endoscope objective optical system shown in FIG. 2A, in a close observation state.

FIGS. 2A and 2B show the overall configuration of an endoscope objective optical system according to Example 1 of the present invention, and lens data is shown below. Furthermore, FIGS. 3A and 3B show aberration curve diagrams of the endoscope objective optical system of this Example.

| lens data | | | | |
|---|---|---|---|---|
| surface number | r | d | Ne | vd |
| 1 | ∞ | 0.27 | 1.85902 | 40.39 |
| 2 | (aspheric surface) | 0.35 | | |
| 3 | ∞ | 0.5 | 1.88815 | 40.76 |
| 4 | −2.081 | d1 | | |
| 5 | ∞ | 0.31 | 1.523 | 65.13 |
| 6 | ∞ | 0 | | |
| 7 | ∞ | 0.03 | | |
| 8 (stop) | ∞ | 0 | | |
| 9 | ∞ | 0.67 | 1.48915 | 70.23 |
| 10 | −5.206 | d2 | | |
| 11 | ∞ | 0.84 | 1.59143 | 61.14 |
| 12 | −1.672 | 0.12 | | |
| 13 | 1.637 | 1.19 | 1.48915 | 70.23 |
| 14 | −1.732 | 0.27 | 2.11729 | 18.05 |
| 15 | (aspheric surface) | 0.46 | | |
| 16 | ∞ | 0.46 | 1.51825 | 64.14 |
| 17 | ∞ | 0.02 | 1.5119 | 64.05 |
| 18 | ∞ | 0.64 | 1.6135 | 50.49 |
| 19 (imaging plane) | ∞ | 0 | | |

-continued

| lens data | |
|---|---|
| various data | |

(second surface)

r = 0.739
k = −2.077
ac4 = 3.7596E−01
ac6 = −1.8226E−01
(fifteenth surface)

r = −7.637
k = −8.876
ac4 = 5.9263E−02
ac6 = −3.6753E−03

| | normal observation state (FIG. 2A) | close observation state (FIG. 2B) |
|---|---|---|
| d0: object distance | 43 | 16.5 |
| d1 | 0.24 | 0.49 |
| d2 | 0.59 | 0.34 |
| F no. | 3.313 | 3.421 |
| f: focal length | 0.996 | 0.964 |
| f2: second-group focal length | | 10.643 |
| l: second-group movement distance | | 0.25 |

Example 2

Figure 4A:
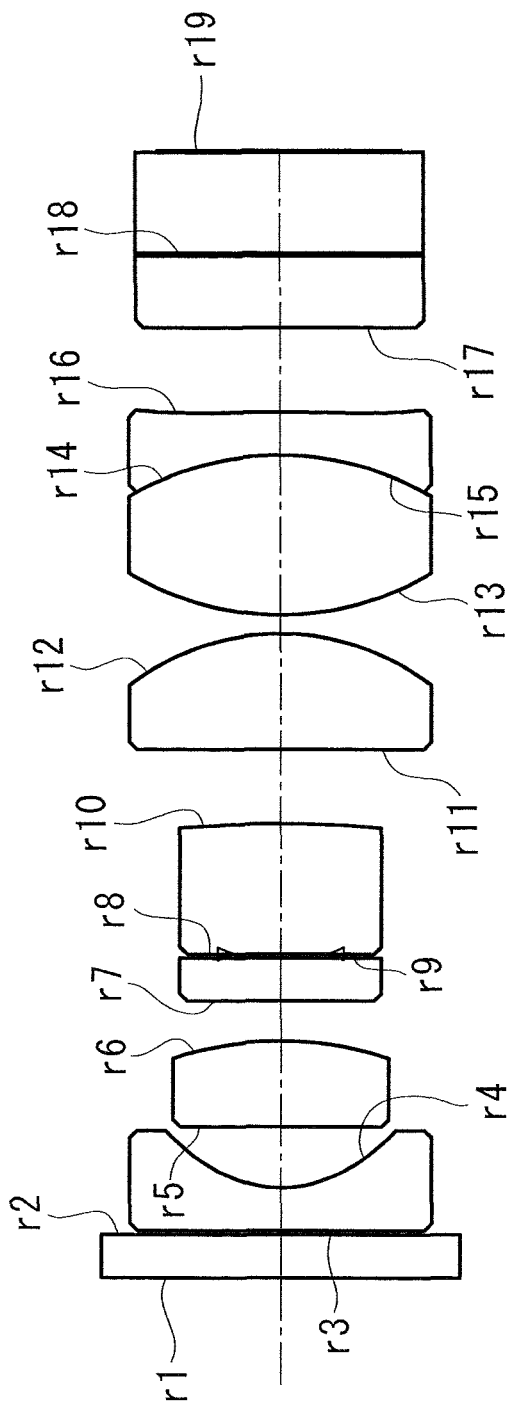
FIG. 4A is a sectional view showing the overall configuration of an endoscope objective optical system according to Example 2 of the present invention, in the normal observation state.
Figure 4B:
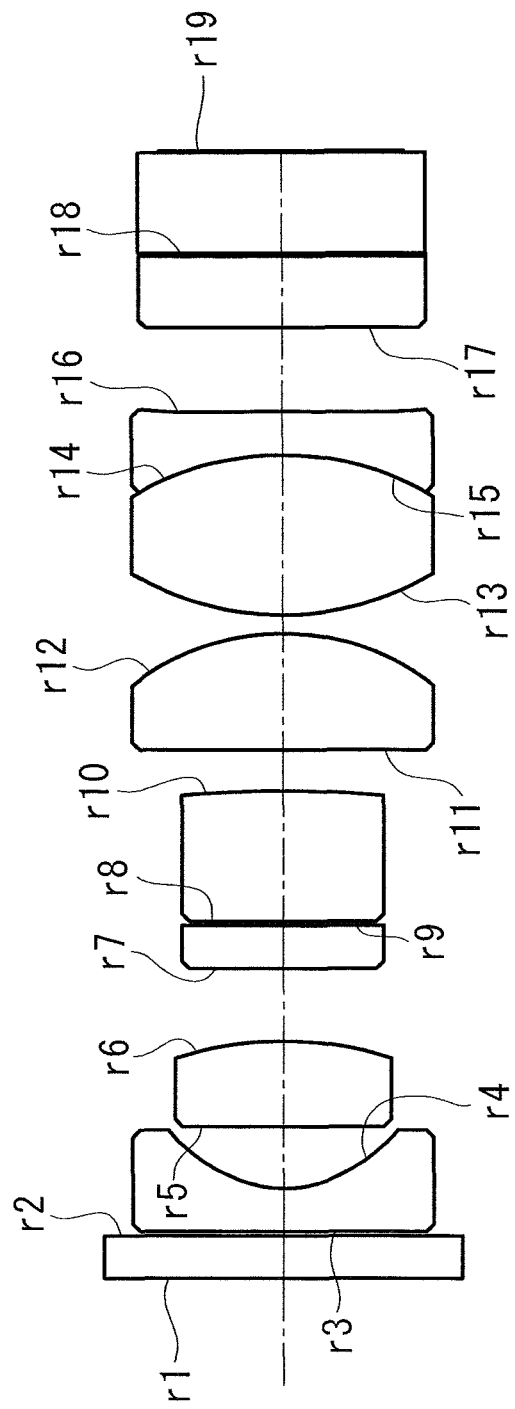
FIG. 4B is a sectional view of the endoscope objective optical system shown in FIG. 4A, in the close observation state.
Figure 5A:
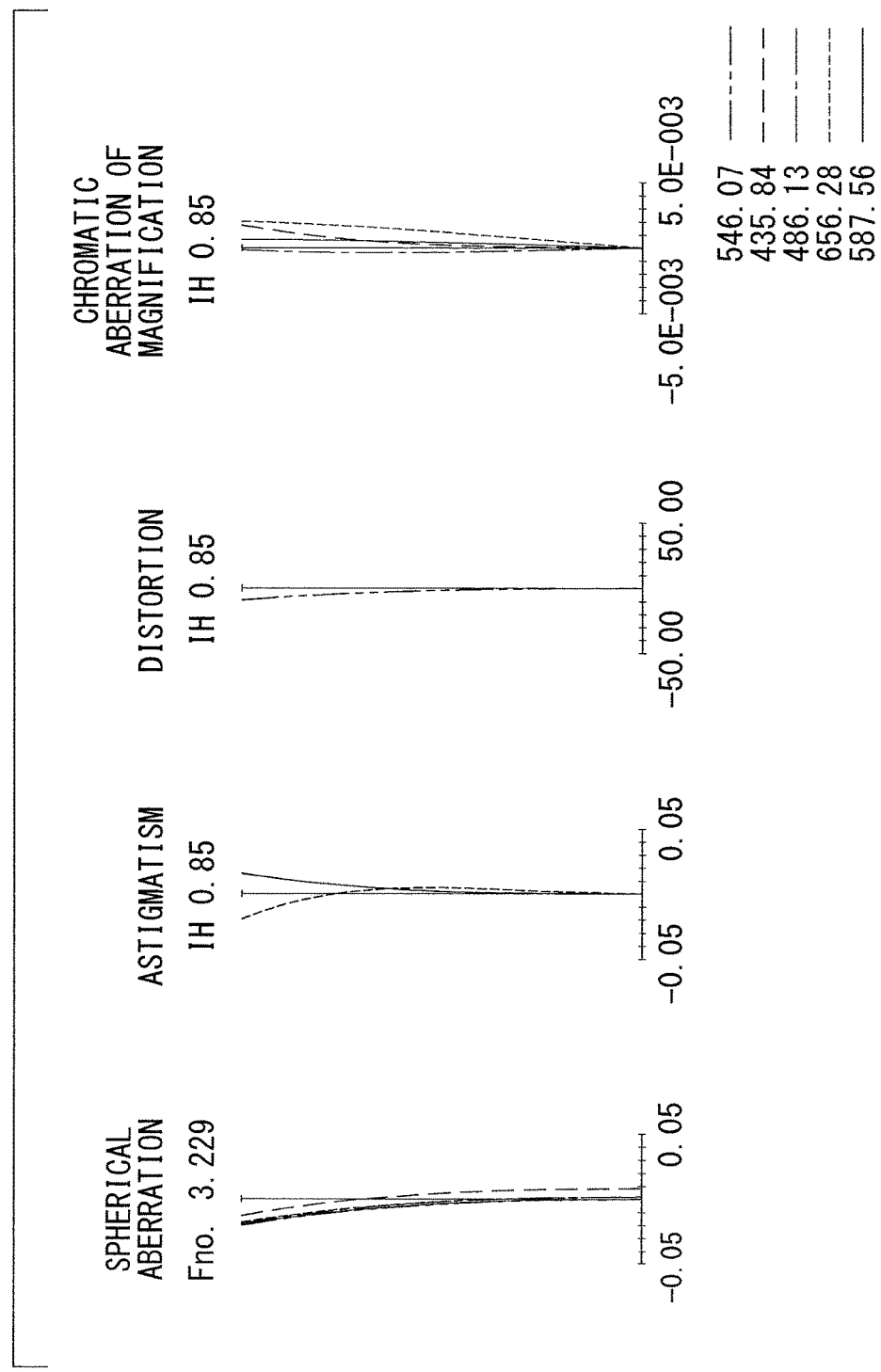
FIG. 5A is an aberration curve diagram of the endoscope objective optical system according to Example 2 of the present invention, in the normal observation state.
Figure 5B:
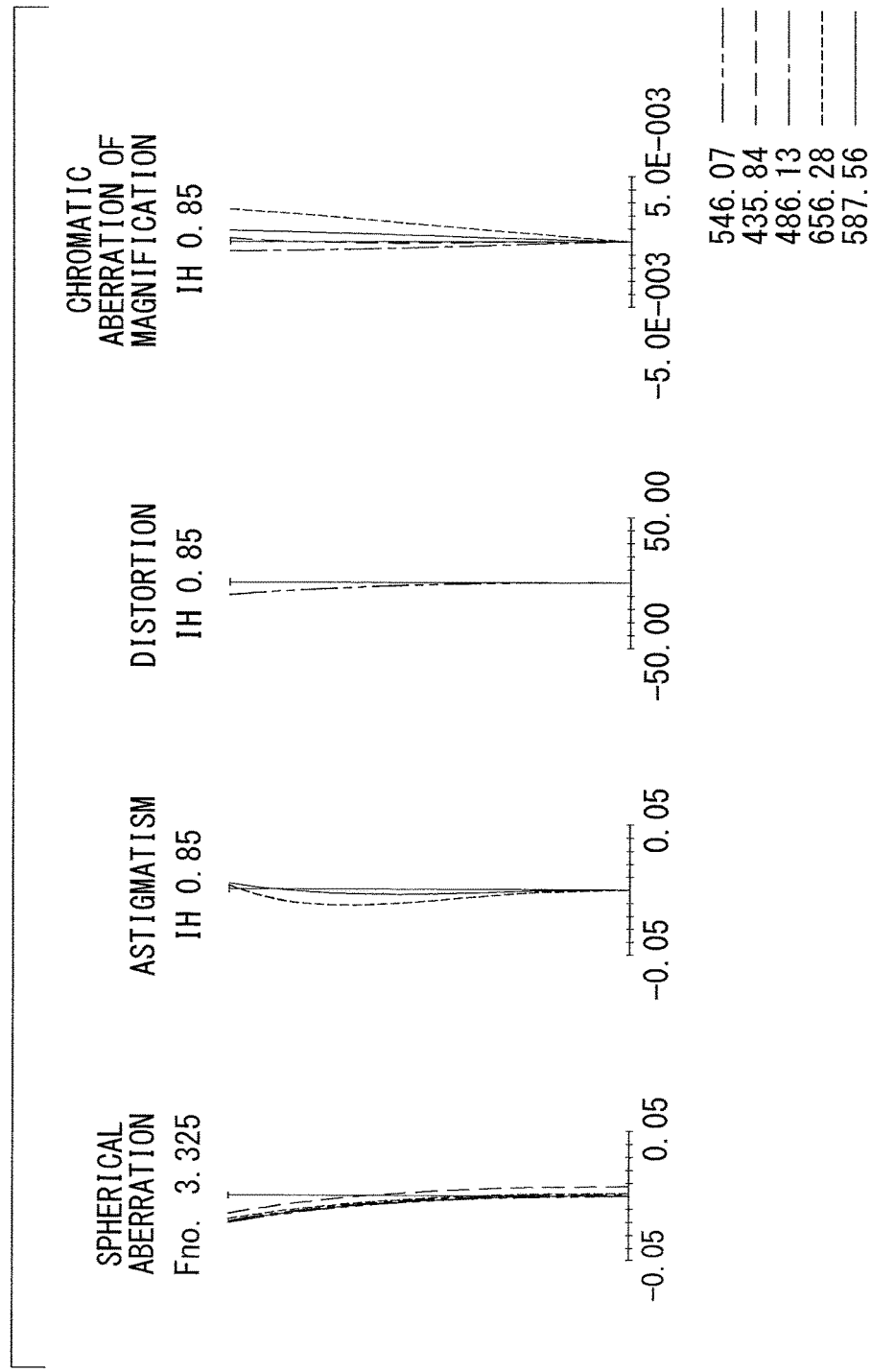
FIG. 5B is an aberration curve diagram of the endoscope objective optical system according to Example 2 of the present invention, in the close observation state.

FIGS. 4A and 4B show the overall configuration of an endoscope objective optical system according to Example 2 of the present invention, and lens data is shown below. Note that, in this Example, a parallel plate is disposed at the object side of the first lens L1. Furthermore, FIGS. 5A and 5B show aberration curve diagrams of the endoscope objective optical system of this Example.

| lens data | | | | |
|---|---|---|---|---|
| surface number | r | d | Ne | vd |
| 1 | ∞ | 0.3 | 1.77066 | 71.79 |
| 2 | ∞ | 0.03 | | |
| 3 | ∞ | 0.3 | 1.85902 | 40.39 |
| 4 | (aspheric surface) | 0.43 | | |
| 5 | ∞ | 0.6 | 1.88815 | 40.76 |
| 6 | −2.414 | d1 | | |
| 7 | ∞ | 0.3 | 1.523 | 65.13 |
| 8 | ∞ | 0.03 | | |
| 9 (stop) | ∞ | 0.91 | 1.48915 | 70.23 |
| 10 | −7.584 | d2 | | |
| 11 | ∞ | 0.81 | 1.59143 | 61.14 |
| 12 | −1.724 | 0.13 | | |
| 13 | 2.079 | 1.11 | 1.59143 | 61.14 |
| 14 | −2.079 | 0.3 | 2.11729 | 18.05 |
| 15 | (aspheric surface) | 0.59 | | |
| 16 | ∞ | 0.5 | 1.51825 | 64.14 |
| 17 | ∞ | 0.02 | 1.5119 | 64.05 |
| 18 | ∞ | 0.7 | 1.6135 | 50.49 |
| 19 (imaging plane) | ∞ | 0 | 0 | |

(fourth surface)

r = 0.834
k = −0.978
ac4 = −3.9082E−02
ac6 = 1.0812E−01
(fifteenth surface)

r = −15.052
k = −58.918
ac4 = 5.1350E−02
ac6 = −6.6229E−03

| | normal observation state (FIG. 4A) | close observation state (FIG. 4B) |
|---|---|---|
| d0: object distance | 38 | 20 |
| d1 | 0.28 | 0.51 |
| d2 | 0.52 | 0.29 |
| F no. | 3.229 | 3.325 |
| f: focal length | 1.002 | 0.982 |
| f2: second-group focal length | | 15.505 |
| l: second-group movement distance | | 0.23 |

Second Embodiment

An endoscope objective optical system according to a second embodiment of the present invention will be described below with reference to the drawings.

As shown in FIG. 6, the endoscope objective optical system is provided with, in order from an object side, a first group G1 having negative refractive power, a second group G2 having positive refractive power, and a third group G3 having positive refractive power, as in the endoscope objective optical system of the above-described first embodiment.

In this embodiment, the lens constitution of the third group G3 differs from that of the third group in the first embodiment. Specifically, the third group G3 in this embodiment is provided with, in order from the object side, a combined lens CL2 in which a fourth lens that is a plano-concave lens having a plane surface at the object side thereof and a fifth lens that is a double-convex lens are combined, and a combined lens CL3 in which a sixth lens that is a double-convex lens and a seventh lens that is a double-concave lens are combined.

The other constitutions are the same as those in the first embodiment; therefore, identical reference signs are assigned thereto, and a description thereof will be omitted.

Example 3

Figure 7A:
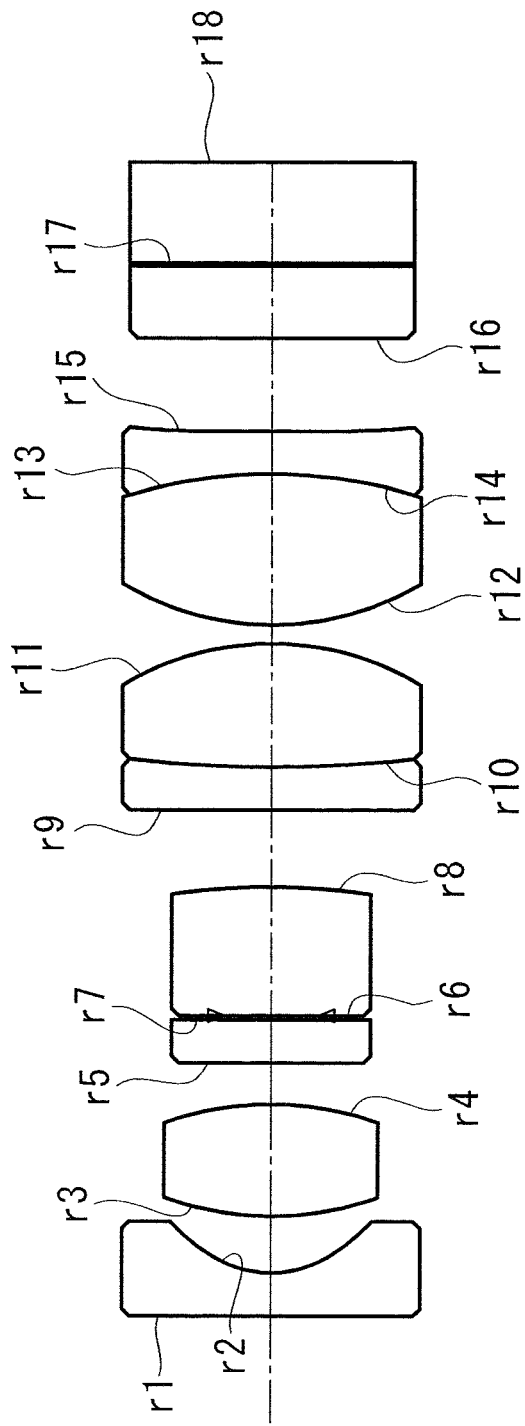
FIG. 7A is a sectional view showing the overall configuration of an endoscope objective optical system according to Example 3 of the present invention, in the normal observation state.

FIGS. 7A and 7B show the overall configuration of an endoscope objective optical system according to Example 3 of the present invention, and lens data is shown below. Furthermore, FIGS. 8A and 8B show aberration curve diagrams of the endoscope objective optical system of this Example.

| lens data | | | | |
|---|---|---|---|---|
| surface number | r | d | Ne | vd |
| 1 | ∞ | 0.3 | 1.85902 | 40.39 |
| 2 | (aspheric surface) | 0.4 | | |
| 3 | 2.248 | 0.78 | 1.59667 | 35.31 |
| 4 | −2.248 | d1 | | |
| 5 | ∞ | 0.3 | 1.523 | 65.13 |
| 6 | ∞ | 0.03 | | |
| 7 (stop) | ∞ | 0.9 | 1.48915 | 70.23 |
| 8 | −4.895 | d2 | | |
| 9 | ∞ | 0.3 | 1.85504 | 23.78 |
| 10 | 8.769 | 0.86 | 1.59143 | 61.14 |
| 11 | −2.032 | 0.13 | | |
| 12 | 2.051 | 1.05 | 1.59143 | 61.14 |
| 13 | −3.419 | 0.3 | 2.11729 | 18.05 |
| 14 | (aspheric surface) | 0.65 | | |
| 15 | ∞ | 0.5 | 1.51825 | 64.14 |
| 16 | ∞ | 0.02 | 1.5119 | 64.05 |

-continued

| lens data | | | | |
|---|---|---|---|---|
| 17 | ∞ | 0.7 | 1.6135 | 50.49 |
| 18 (imaging plane) | ∞ | | | |

(second surface)

r = 0.702
k = −1.36
ac4 = 1.4058E−01
ac6 = −2.0620E−03
(fourteenth surface)

r = −55.087
k = 0.264
ac4 = 3.7398E−02
ac6 = −5.0443E−04

| | normal observation state (FIG. 7A) | close observation state (FIG. 7B) |
|---|---|---|
| d0: object distance | 40 | 20 |
| d1 | 0.29 | 0.5 |
| d2 | 0.54 | 0.33 |
| F no. | 3.261 | 3.297 |
| f: focal length | 0.997 | 0.972 |

| | | |
|---|---|---|
| f2: second-group focal length | | 10.007 |
| l: second-group movement distance | | 0.21 |

Example 4

Figure 9A:
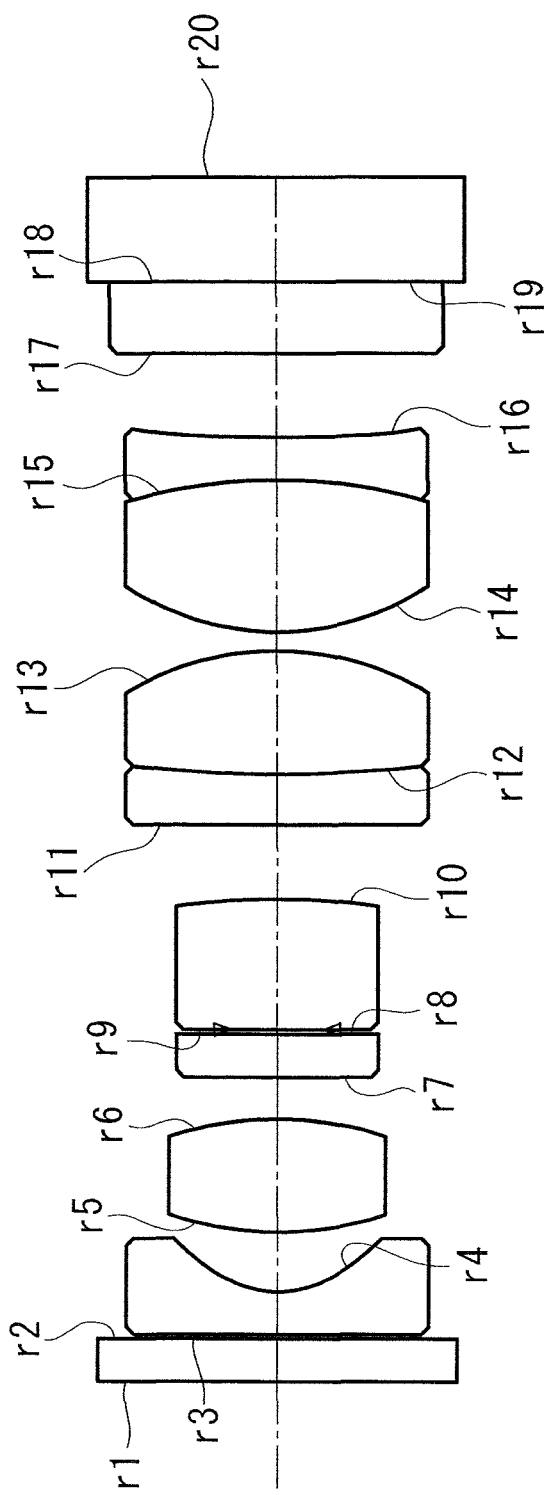
FIG. 9A is a sectional view showing the overall configuration of an endoscope objective optical system according to Example 4 of the present invention, in the normal observation state.
Figure 9B:
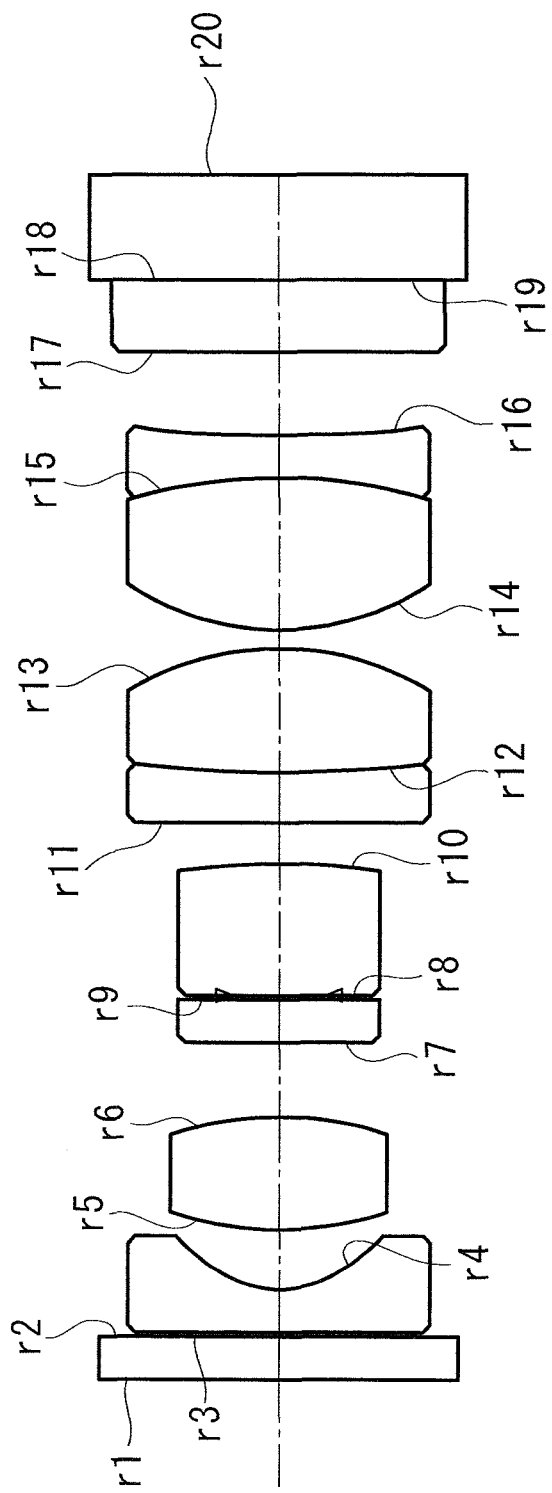
FIG. 9B is a sectional view of the endoscope objective optical system shown in FIG. 9A, in the close observation state.
Figure 10B:
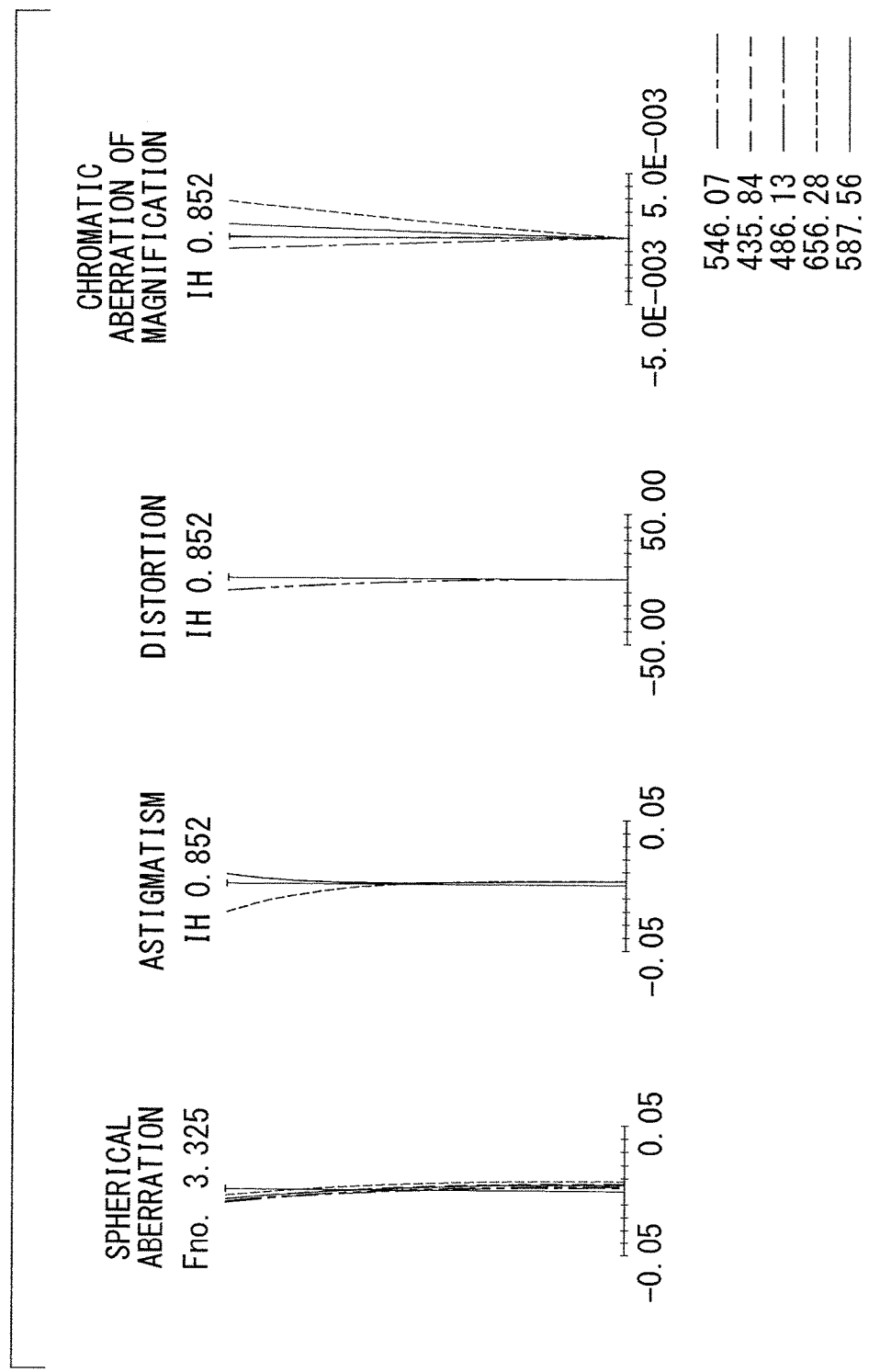
FIG. 10B is an aberration curve diagram of the endoscope objective optical system according to Example 4 of the present invention, in the close observation state.

FIGS. 9A and 9B show the overall configuration of an endoscope objective optical system according to Example 4 of the present invention, and lens data is shown below. Note that, in this Example, a parallel plate is disposed at the object side of the first lens L1. Furthermore, FIGS. 10A and 10B show aberration curve diagrams of the endoscope objective optical system of this Example.

| lens data | | | | |
|---|---|---|---|---|
| surface number | r | d | Ne | vd |
| 1 | ∞ | 0.3 | 1.77066 | 71.79 |
| 2 | ∞ | 0.03 | | |
| 3 | ∞ | 0.3 | 1.85902 | 40.39 |
| 4 | (aspheric surface) | 0.42 | | |
| 5 | 2.39 | 0.79 | 1.62409 | 36.26 |
| 6 | −2.39 | d1 | | |
| 7 | ∞ | 0.3 | 1.523 | 65.13 |
| 8 | ∞ | 0.0302 | | |
| 9 (stop) | ∞ | 0.92 | 1.48915 | 70.23 |
| 10 | −4.829 | d2 | | |
| 11 | ∞ | 0.35 | 1.85504 | 23.78 |
| 12 | 8.877 | 0.86 | 1.59143 | 61.14 |
| 13 | −2.057 | 0.13 | | |
| 14 | 1.92 | 1.06 | 1.59143 | 61.14 |
| 15 | −3.755 | 0.3 | 2.11729 | 18.05 |
| 16 | (aspheric surface) | 0.58 | | |
| 17 | ∞ | 0.5 | 1.51825 | 64.14 |
| 18 | ∞ | 0.02 | 1.5119 | 64.05 |
| 19 | ∞ | 0.71 | 1.6135 | 50.49 |
| 20 (imaging plane) | ∞ | | | | various data (fourth surface)

r = 0.715
k = −1.362

-continued

| lens data |
|---|
| ac4 = 1.3095E−01 |
| ac6 = −6.8907E−03 |
| (fifteenth surface) | r = 37.135
k = 0.019
ac4 = 4.3109E−02
ac6 = 6.6393E−04

| | normal observation state (FIG. 9A) | close observation state (FIG. 9B) |
|---|---|---|
| d0 | 40 | 20 |
| d1 | 0.29 | 0.52 |
| d2 | 0.52 | 0.29 |
| F no. | 3.218 | 3.252 |
| f: focal length | 0.997 | 0.970 |

| | |
|---|---|
| f2: second-group focal length | 9.872 |
| l: second-group movement distance | 0.23 |

Note that Table 1 shows values of the above-described conditional expressions (1) to (3) in the endoscope objective optical systems of the above-described Examples 1 to 4.

TABLE 1

| | Example 1 | Example 2 | Example 3 | Example 4 |
|---|---|---|---|---|
| Conditional Expression (1) | 10.691 | 15.467 | 10.037 | 9.899 |
| Conditional Expression (2) | 0.251 | 0.229 | 0.211 | 0.231 |
| Conditional Expression (3) | 2.61 | 1.90 | 2.00 | 2.00 |

As a result, the above-described embodiments lead to the following aspect.

An aspect of the present invention is directed to an endoscope optical system of the present invention including, in order from an object side, a first group having negative refractive power, a second group having positive refractive power, and a third group having positive refractive power, wherein the second group moves in an optical-axis direction to perform focusing for a normal observation state and a close observation state; and the following conditional expression is satisfied, $$9 < f2/fa < 16 \quad (1)$$

where f2 is a focal length of the second group, and fa is a focal length of the entire system in the normal observation state.

According to the above-described configuration, the endoscope objective optical system satisfies the conditional expression (1), thereby suppressing a fluctuation in the angle of view caused when the second group is moved in the optical-axis direction, i.e., at the time of focusing, and the movement distance of the second group is made to fall within an appropriate range to allow the entire length of the endoscope objective optical system to be an appropriate length, thereby not impairing the operability of an endoscope.

When the power of the second group becomes less than the lower limit of the conditional expression (1), there is a possibility that a fluctuation in the angle of view becomes large, and thus, a user experiences a feeling of strangeness due to a change in the image at the time of focusing. On the other hand, when the power of the second group becomes greater than the upper limit of the conditional expression (1), the movement distance of the second group for focusing is increased, thus increasing the entire length of the optical system. Accordingly, in an insertion portion of an endoscope to which the endoscope objective optical system is applied, a distal-end rigid section thereof is lengthened, thus deteriorating the usability of the endoscope.

In the above-described configuration, it is preferred that the following conditional expression be satisfied, $$0.2 < l/fa < 0.3 \quad (2)$$

where l is a movement distance of the second group associated with focusing, and fa is a focal length of the entire system in the normal observation state.

The conditional expression (2) is a conditional expression for defining the movement distance of the second group at the time of focusing. When the movement distance of the second group becomes less than the lower limit of the conditional expression (2), an error due to variations among parts becomes large, and thus, focus adjustment is required both in the normal observation state and in the close observation state. In short, the focus adjustment work at the time of assembly becomes cumbersome. On the other hand, when the movement distance of the second group becomes greater than the upper limit of the conditional expression (2), the entire length of the optical system is increased, and thus, in an insertion portion of an endoscope to which the endoscope objective optical system is applied, a distal-end rigid section thereof is lengthened, thus deteriorating the usability of the endoscope.

In the above-described configuration, it is preferred that the lens that constitutes the second group be formed of a single plano-convex lens.

Although there is a case in which various filters are provided in an optical system for an endoscope, the second group is formed of a single plano-convex lens, thereby making it possible to dispose an optical filter suitable for an intended purpose, at the plane-surface side of the plano-convex lens. In short, the second group is formed of a single plano-convex lens, thereby making it possible to provide a parallel-plate light filter without making the frame configuration complicated and without increasing the number of parts.

Example light filters include: a laser cut filter that is used to prevent a situation in which, when a laser probe is inserted from a forceps opening in an endoscope to perform treatment using laser light, a screen becomes too bright by the laser light, thus making it difficult to observe a subject; and a color correction filter that is used to correct the difference in color due to the spectral sensitivity of an imaging device.

Furthermore, an aperture stop can be provided between the plano-convex lens and the light filter. Because the ray height becomes low in the vicinity of the aperture stop, the aperture stop is set as a member between the plano-convex lens and the light filter, thereby making it possible to reduce the diameter of the lens of the second group, and thus, the second moving group including the frame can be reduced in size and weight.

In the above-described configuration, it is preferred that the following conditional expression be satisfied, $$1.3 < d0a/d0b < 3.5 \quad (3)$$

where d0a is an object distance in the normal observation state, and d0b is an object distance in the close observation state. Here, the object distance is the distance to an object from a surface of the endoscope objective optical system that is closest to the object, when the imaging plane is located at a position where the MTF at an evaluation frequency determined by the pixel pitch and the imaging method of an imaging device becomes maximum.

The conditional expression (3) is a conditional expression for defining a change in object distance caused by focusing. When d0a/d0b is less than the lower limit of the conditional expression (3), a change in the observation depth caused by focusing is small, and the observable range, which is obtained by adding the observation depths in the normal observation state and in the close observation state, is narrowed. On the other hand, when d0a/d0b exceeds the upper limit of the conditional expression (3), the out-of-focus distance range in the normal observation state and in the close observation state is produced between the observation depth in the normal observation state and the observation depth in the close observation state, which causes a disadvantage for observation and treatment.

According to the present invention, an advantageous effect is afforded in that it is possible to provide an endoscope objective optical system that is capable of performing focusing according to the distance to an object to be observed, in which a fluctuation in the angle of view caused by focusing is small, and in which a variation in the observation depth is small, while allowing easy focus adjustment.

REFERENCE SIGNS LIST

G1 first group
G2 second group
G3 third group
L1 first lens
L2 second lens
L3 third lens
L4 fourth lens
L5 fifth lens
L6 sixth lens
L7 seventh lens
CL1 combined lens
CL2 combined lens
CL3 combined lens
LF light filter
S aperture stop
CG cover glass
I imaging plane

The invention claimed is:

1. An endoscope objective optical system consisting of, in order from an object side, a first group having negative refractive power, a second group having positive refractive power, and a third group having positive refractive power,
   wherein the second group comprises a single plano-convex lens and moves in an optical-axis direction to perform focusing from a normal observation state to a close observation state, wherein all other lens elements within the objective optical system are stationary during focusing; and
   wherein the following conditional expression is satisfied, $$9 < f2/fa < 16 \quad (1)$$

where f2 is a focal length of the second group, and fa is a focal length of the entire system in the normal observation state.

2. An endoscope objective optical system according to claim 1, wherein the following conditional expression is satisfied, $$0.2 < l/fa < 0.3 \quad (2)$$

where l is a movement distance of the second group associated with focusing, and fa is a focal length of the entire system in the normal observation state.

3. An endoscope objective optical system according to claim 2, wherein the following conditional expression is satisfied, $$1.3 < d0a/d0b < 3.5 \tag{3}$$

where d0a is an object distance in the normal observation state, and d0b is an object distance in the close observation state.

* * * * *